United States Patent
McFarland et al.

(10) Patent No.: US 7,291,118 B2
(45) Date of Patent: Nov. 6, 2007

(54) METHOD FOR DETERMINING THE RISK OF DEVELOPING A SKELETAL CONDITION

(75) Inventors: David H. McFarland, Town of Mount Royal (CA); Tracey A. McCulloch, Montreal (CA); Timothy K. Woo, Montreal (CA); Sylvain Guimond, Ste-Anne de Sorel (CA)

(73) Assignee: Biotonix Inc., Montreal, Quebec ( * ) Notice: Subject to any disclaimer, the term of this patent is extended or adjusted under 35 U.S.C. 154(b) by 0 days.

(21) Appl. No.: 10/234,964

(22) Filed: Sep. 5, 2002

(65) Prior Publication Data

US 2004/0049103 A1    Mar. 11, 2004

(51) Int. Cl.
*A61B 5/103*    (2006.01)

(52) U.S. Cl. ..................... 600/587; 600/594

(58) Field of Classification Search ............. 600/587, 600/594, 595; 482/8, 9; 128/920, 923
See application file for complete search history.

(56) References Cited

U.S. PATENT DOCUMENTS

| | | | | |
|---|---|---|---|---|
| 4,760,851 | A * | 8/1988 | Fraser et al. ............. | 600/587 |
| 4,971,069 | A * | 11/1990 | Gracovetsky ........... | 600/594 |
| 5,080,109 | A * | 1/1992 | Arme, Jr. ................ | 600/595 |
| 6,007,459 | A * | 12/1999 | Burgess .................. | 482/4 |
| 6,190,287 | B1 * | 2/2001 | Nashner .................. | 482/8 |
| 6,387,061 | B1 * | 5/2002 | Nitto ...................... | 600/587 |
| 6,514,219 | B1 * | 2/2003 | Guimond et al. ........ | 600/595 |
| 6,524,260 | B2 * | 2/2003 | Shechtman et al. ...... | 600/594 |
| 6,565,519 | B2 * | 5/2003 | Benesh .................... | 600/587 |

OTHER PUBLICATIONS

Mehrsheed Sinai et al., Am. J. Phys, Med. Rhabil. vol. 75, Sep./Oct. 1995, pp. 370-374.
David Levine et al., JOSPT, Research Study, vol. 24, No. 3, Sep. 1996, pp. 130-135.
J.B, Lauritzen, Elsevier, Bone vol. 18, No. 1, Supplement Jan. 1996-, pp. 65S-75S.
M. Cohen-Solal et al., Journal of Bone and Mineral Research, vol. 18, Nov. 11, 2003, pp. 1989-1994.
R.C, Puche et al., Elsevier, Bone vol. 17, No. 3, Sep. 1995, pp. 239-246.
Philip D. Ross et al., American College of Physicians, Annals of Internal Medicine, vol. 114, No. 11, Jun. 1, 1991, pp. 919-923.
K.P. Singer et al., SPINE vol. 19, No. 12, 1994, pp. 1381-1384.
Warren A. Katz, The Physician and Sportsmedicine, vol. 26, No. 2, Feb. 1998, pp. 1-9.

(Continued)

*Primary Examiner*—Charles Marmor
(74) *Attorney, Agent, or Firm*—Fay Kaplun & Marcin, LLP

(57) ABSTRACT

The present invention relates to a method and apparatus for calculating postural deviation values indicative of a skeletal condition risk in a patient including the steps of obtaining position data identifying a position in space of body landmarks of an upper body of a patient while standing relaxed and in normal posture; obtaining weight data of the patient; calculating vertical and horizontal plumb line using the position data; and calculating angle deviation values of body parts of the patient being indicative of a skeletal condition risk with respect to the plumb line position value using the position data.

26 Claims, 5 Drawing Sheets

OTHER PUBLICATIONS

JAMA, Jan. 20, 1999, vol. 281, No. 3, Osteoporosis Among Estrogen-Deficient Women, Summary of MMWR, 1998:47-969-973, pp. 224-226.

The Canadian Consensus on Menopause and Osteoporosis, No. 108, Sep. 2001.

Chui Kin Yuen et al., Canadian Consensus on Menopause and Osteoporosis, pp. 1-11.

Is There a Role for Exercise in the prevention of Osteoporosis Fractures, J. Sports Med. 1999-33 pp. 378-386.

Richard S. Kaplan et al., Mayo Clin. Proc. 1993 . vol. 68, pp. 171-1176.

Mehrsheed Sinaki et al., Mayo Clin. Proc. 1996, vol. 71, pp. 951-956.

Eiji Itoi et al., Mayo Clin. Proc. 1994. vol. 69, pp. 1054-1059.

Warren A. Katz et al., The Physician and Sportsmedicine, vol. 26, No. 2, Feb. 1998, pp. 33-43.

American College of Sports Medicine, "Osteoporosis and Exercise", MSSE.27:4 pp. i-vii; 1995.

Warren A. Katz, Exercise Is Medicine, Patient Adviser, vol. 26, No. 2, 1998 pp. 1-3.

Sinaki and Lynn, American Journal of Physical Medicine & Rehabilitation, vol. 81, No. 4, "Reducing the Risk of Falls Through Proprioceptive Dynamic Posture Training in Osteoporosis Women with Kyphotic Posturing" A Randomised Pilot Study, pp. 241-246, 2002.

Mehrsheed Sinaki et al., Arch. Phys. Med. Rehabil., vol. 65, Oct. 1984, pp. 593-596.

Kristine E. Ensrud et al., JAGS, vol. 45 No. 6, 1997, pp. 682-687.

Barbara Lafferty et al., Arch. Phys. Med. Rehabil., vol. 70, Apr. 1989, pp. 322-329.

Eiji Itoi, "Roentgenographic Analysis of Posture in Spinal Osteoporotics" SPINE, vol. 16, No. 7, 1991, pp. 750-756.

Anne Leath Harrison et al., Journal of Spinal Disorders & Techniques, vol. 23, No. 6, Jun. 1996, pp. 353-361.

Bernard Cortet, SPINE, 1999, vol. 24, No. 18, pp. 1921-1925.

Raphael K. Chow et al., American Journal of Physical Medicine, vol. 66, No. 5, pp. 219-226, 1987.

Deed E. Harrison, Journal of Spinal Disorders & Techniques, 2002, vol. 15, No. 3, pp. 213-220.

Elsie G. Culham et al., SPINE, 1994, vol. 19, No. 11, pp. 1250-1255.

Mehrsheed Sinaki, Arch Phys. Med. Rehabil., Mar. 1989, vol. 70, pp. 220-229.

Kerry L. Hertel et al., Nursing Clinics of North America, vol. 36, No. 3, Sep. 2001, pp. 441-453.

\* cited by examiner

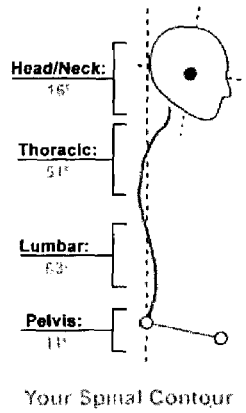
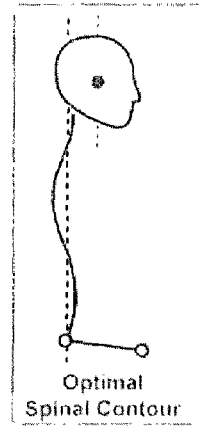

Lily Niedbalsky
June 16 2002

Head/Neck:
16°

Thoracic:

Lumbar:

Pelvis:

Your Spinal Contour

Optimal
Spinal Contour

OPIX

Osteoporosis Postural Index

Your head is 16° from normal.

Your thoracic curve is 13° from normal.
A deviation of X% from normal is indicative of kyphosis.

Your lumbar curve is 4° from normal.
A deviation of X% from normal is indicative of lordosis.

Your pelvis is 10° from normal.

Osteoporosis Risk Index

Low risk of osteoporosis

Fracture Risk Index

Low risk of fracture

Tracking Your Spinal Contour:

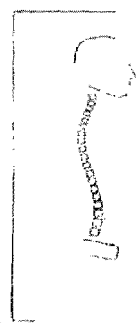

21°
57°
60°
12°

Your Spine on
June 14th 2001

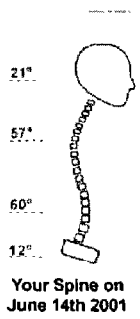

16°
61°
63°
11°

Your Spine on
June 16th 2002

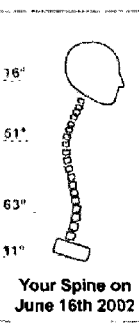

Your next print on
June 14th 2003

COPYRIGHT © MOTIONIX 2002

*Osteoprint* page 3

Fig. 3

METHOD FOR DETERMINING THE RISK OF DEVELOPING A SKELETAL CONDITION

BACKGROUND OF THE INVENTION (a) Field of the Invention

This invention relates a method and apparatus for determining a risk factor indicative of a predisposition to develop a skeletal condition as osteoporosis or a fracture.

(b) Description of Prior Art

Osteoporosis is known as the silent disease. It is characterized by progressive bone thinning leading to fragility and fracture. It is often only diagnosed once a fracture has been experienced. More than 25 million Americans are affected, 80% of whom are women. It has been estimated that one out of every two women and one out of every five men will experience an Osteoporosis-related fracture sometime in their life. By age 75, one third of all men will be affected by Osteoporosis. Estimated direct expenditures (hospitals and nursing homes) in the U.S. for osteoporosis and related fractures are $14 billion each year.

SUMMARY OF THE INVENTION

It is an object of the invention to provide a method and apparatus for determining a risk factor indicative of a predisposition to develop a skeletal condition as osteoporosis or a fracture.

The present invention is related to a biomechanical assessment system that analyzes posture. It helps to identify the postural indicators that are associated with a predisposition to a skeletal condition as osteoporosis to provide early detection and minimize the consequences of this disease.

The skeleton is comprised of a network of bones connected by tendons and ligaments, surrounded by muscle. The strength and integrity of this skeletal system enables us to function well. Bones store calcium, help protect the body from injury, produce blood cells and house the brain and the central nervous system. The skeletal system serves as the framework to support the body, with the bones of the legs and the back supporting body weight.

Posture is a significant indicator of the health of our skeletal frame. An optimum posture would have a plumb line (like the lines used in building) dropping from the level of your ear straight to your shoulder, lining up through the middle of your pelvis, knees and feet. The head, trunk, pelvis and knees are "stacked", one on top of the other. Any deviation from this position can negatively affect health and well-being. Certain postural asymmetries may particularly indicate a risk for Osteoporosis and may contribute to an increased risk of associated fracture.

One object of the present invention is to detect and highlight the postural indicators that identify predisposition to osteoporosis to provide an early detection and to minimize the consequences of this disease.

Another object of the present invention is to detect and highlight the postural indicators that identify a predisposition to risk of fracture due to osteoporosis and minimize risk of fracture through corrective exercise regimes.

The invention improves the accuracy, objectivity and/or simplicity of obtaining data that can be used in diagnosis of osteoporosis. The invention provides better selection of exercises useful in the treatment of osteoporosis. The invention also improves confidence, with the patient and/or the physician, that exercises used to treat osteoporosis are having a continued positive effect.

In accordance with the present invention, there is provided a method and apparatus for determining a risk factor indicative of a predisposition to develop a skeletal condition as osteoporosis or a fracture.

According to one broad aspect of the present invention, there is provided a method for calculating postural deviation values indicative of a skeletal condition risk in a patient comprising the steps of: a) obtaining position data identifying a position in the space of body landmarks of upper body of a patient while standing relaxed and in normal posture; b) obtaining weight data of the patient; c) calculating vertical and horizontal plumb line using the position data; d) calculating angle deviations values of body parts of the patient being indicative of a skeletal condition risk with respect to the plumb line position value using the position data.

According to another broad aspect of the present invention, there is provided a method of selecting exercises for reducing risk to develop a skeletal condition in a patient, the method comprising the steps of: a) obtaining angle deviations of body part of a patient indicative of a risk to develop a skeletal condition; b) correlating angle deviations with exercises for strengthening or stretching specific muscles or muscle groups; c) compiling an exercise program based on the exercises provided in step b).

According to still another broad aspect of the present invention, there is provided an apparatus for calculating postural deviation values indicative of a skeletal condition risk in a patient comprising: a) position data acquisition device for identifying a position in space of body landmarks of upper body of the patient while standing relaxed and in normal posture; b) weight data acquisition device for obtaining weight data of the patient; c) vertical and horizontal plumb line determination device using the position data; d) angle of deviation calculator for determining angle deviation values of body parts being indicative of a skeletal condition risk with respect to the plumb line position value using the position data.

According to a further broad aspect of the present invention, there is provided an apparatus for selecting exercises for reducing risk to develop a skeletal condition in a patient comprising: a) a angle of deviation device for obtaining angle deviations of upper body part of a patient being indicative of a risk to develop a skeletal condition; b) a correlator for correlating angle deviations with exercises for strengthening or stretching muscles or muscle groups; c) a compiler for compiling an exercise program based on the exercises provided by the correlator.

BRIEF DESCRIPTION OF THE DRAWINGS

These and other features, aspects and advantages of the present invention will become better understood with regard to the following description and accompanying drawings wherein:

FIG. 3 illustrates an example of the assessment report of one embodiment of the present invention;

DETAILED DESCRIPTION OF THE INVENTION

In accordance with the present invention, there is provided a method and apparatus for determining a risk factor indicative of a predisposition to develop a skeletal condition as osteoporosis or a fracture.

The present invention is designed to identify the potential for Osteoporosis and to serve as an early warning or screening tool. Posture is examined by means of a lateral view photo. Spinal contour is extracted from the digital image, sent via the web to a central server and software is used to detect postural deviations of various body segments and compare them to established norms. An Osteoporosis Postural Index (OPIX) is formed summarizing the postural orientations of different body segments. This provides the input stage to an expert system designed to weight the body segment and deviation magnitudes from normal and to form two related indices: risk of osteoporosis and risk of bone fracture related to osteoporosis.

The Osteoporosis Index is designed to identify if a patient's posture is associated with Osteoporosis, and the Risk Fracture Index indicates the potential for fractures. This screening tool leads to early detection and treatment to minimize the consequences of osteoporosis. Beyond the screening function of the risk assessment report, corrective exercises are available to the healthcare practitioner that target the specific postural deviations individually identified in the osteoporitic patient, with the goal of minimizing risk of fracture and improving daily living.

An expert database is formed of various postural parameters associated with osteoporosis further refining the detection capabilities of the system and improving its role as an early warning/screening device.

Six, light-reflective markers (1 flat and 5 spherical) will be placed on well-defined anatomical landmarks. More specifically, markers will be placed over the tragus (flat marker), acromion. C7, T5, Anterior-superior iliac spine (ASIS), and Posterior-superior iliac spine (PSIS). The positioning of the markers and the obtention of their space position is more detailed in U.S. Pat. No. 6,514,219 which is incorporated by reference and in the International Patent Application No. PCT/CA01/01649.

Digital photograph is taken of the client against a calibrated backdrop.

Photo is loaded into the computer, indwelling software is used to scan the image, extract the spinal contour and marker locations, and transmit the data via the Internet to a central server for processing.

Head angle, pelvic tilt and kyphosis and lordosis (the latter highly indicative of osteoporosis) are calculated.

The marker orientation (in angles) relative to vertical (head) and horizontal (pelvic) plumb lines are calculated.

Figure 1:
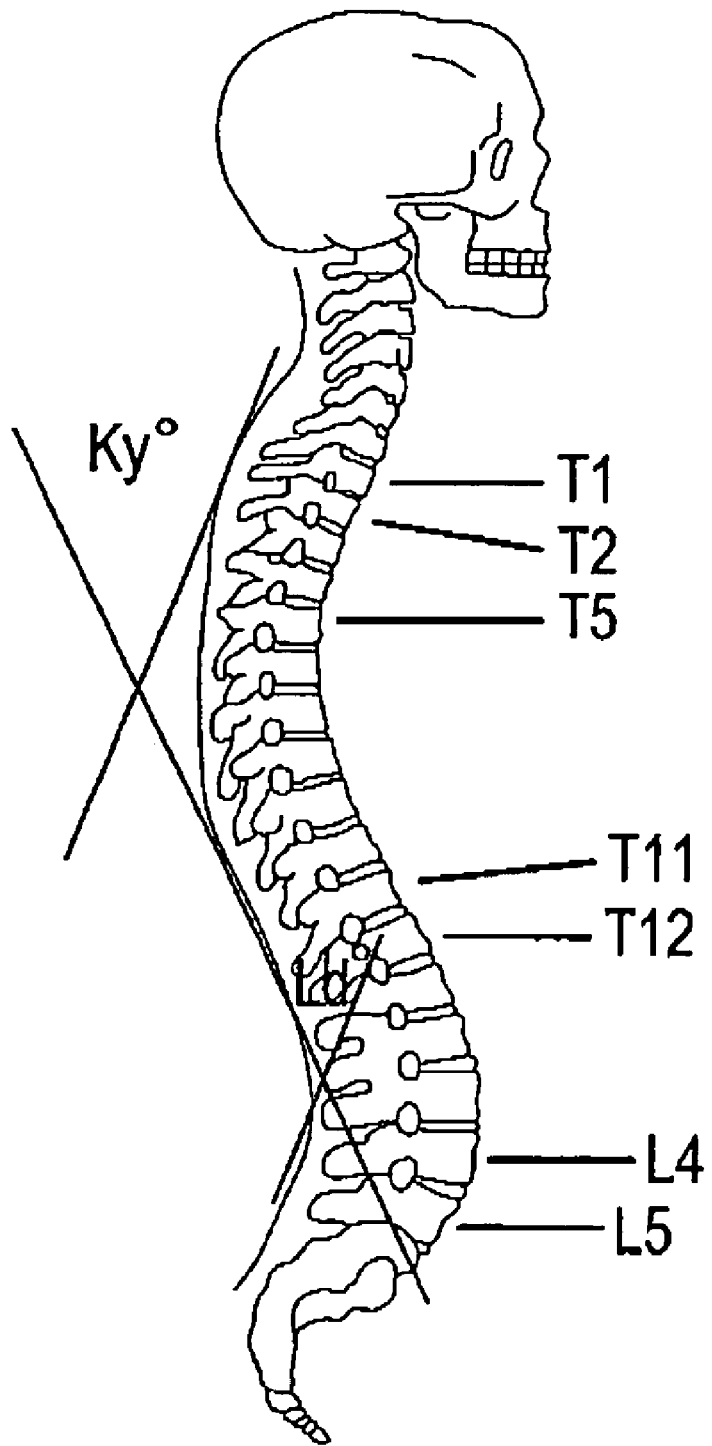
FIG. 1 illustrates the contour silhouette of the back of a patient and the lines extrapolated from the upper thoracic vertebrae (T1) and the lower thoracic vertebrae (T2)
Figure 2:
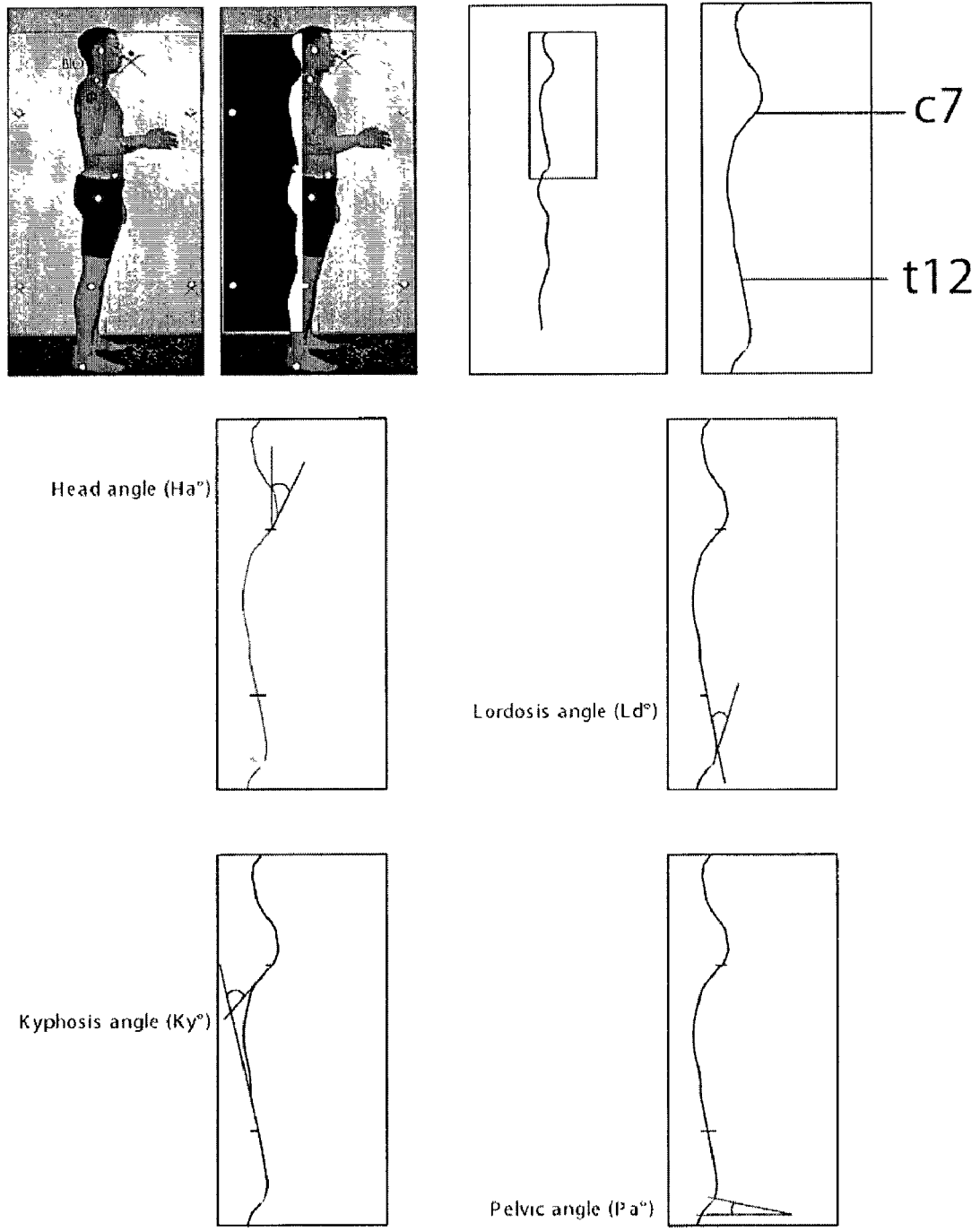
FIG. 2 illustrates the calculation of the head angle, lordosis angle, kyphosis angle and pelvic angle.
Figure 4:
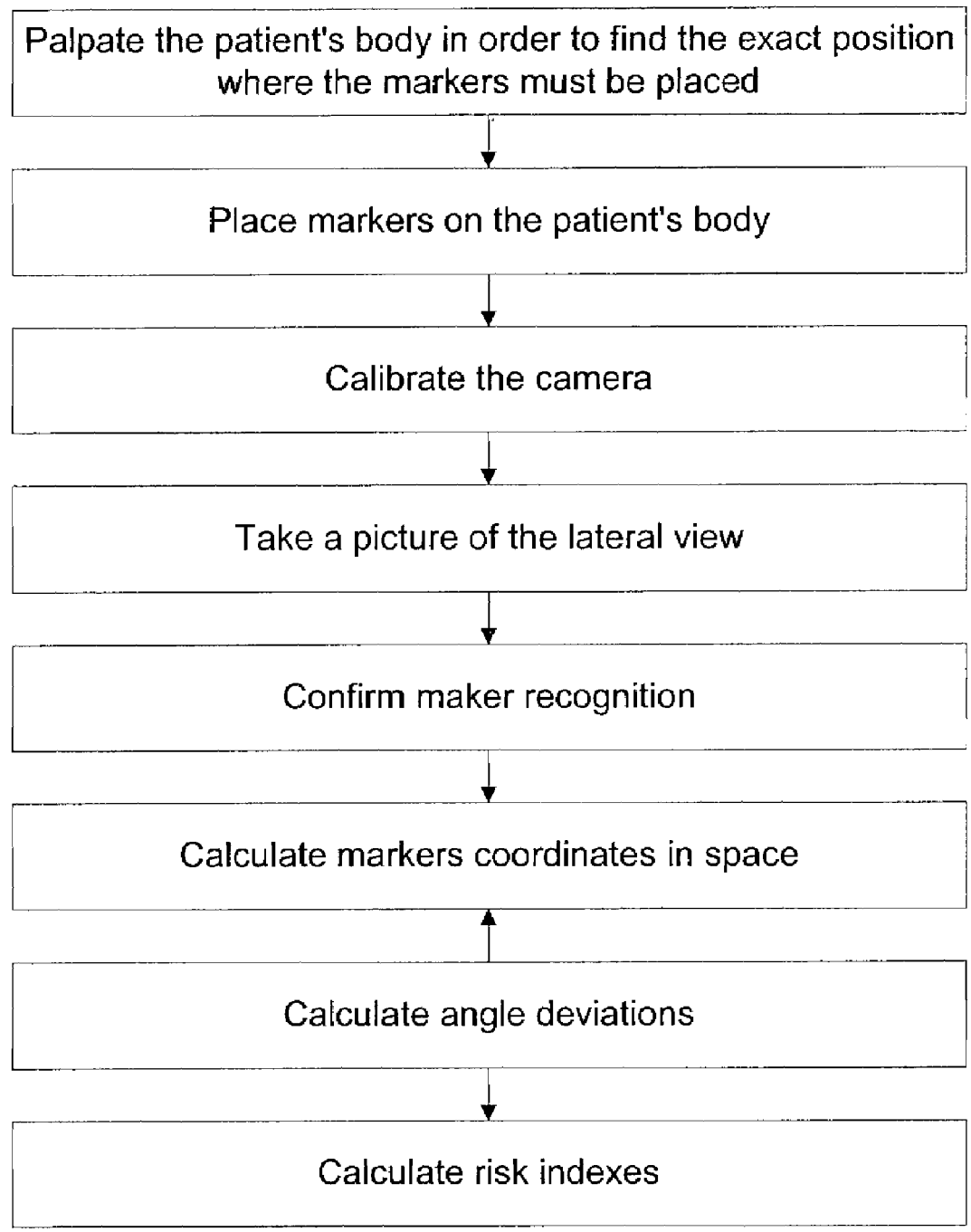
FIG. 4 is a block diagram of the method for assessing a risk of developing a skeletal condition of a preferred embodiment of the present invention.
Figure 5:
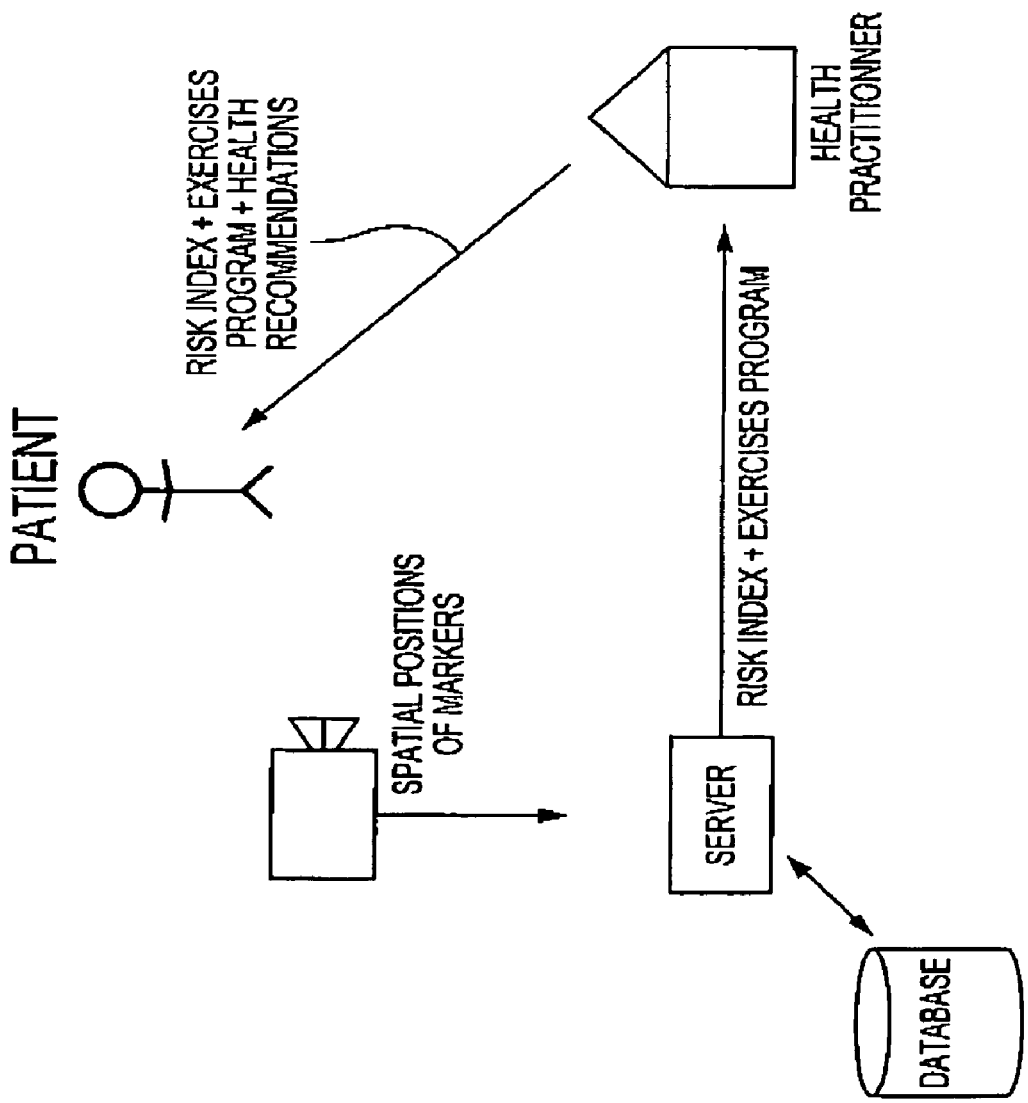
FIG. 5 is a schema of the system of a preferred embodiment of the present invention.

A contour silhouette of the back in the lateral view is used to calculate Kyphosis and lordosis Two lines are extrapolated from the contour mapping the upper thoracic vertebrae (T1, T2) and the lower thoracic vertebrae (T11, T12) (FIG. 1). An angle (ky°) is measured from these two lines to give an index of kyphosis. Norms exist for comparisons to measured variables. Lordosis is measured (Ld°) similarly using the lower thoracic vertebrae (T1, T12) and the lower lumbar vertebrae (L4, L5). T12 is estimated using the location of T5. The distance from T1 to T5 is approximately 30% of the distance from T1 to T12 (FIG. 2).

In the event the subject has excess fatty tissue around the abdominal area that may obscure the contour silhouette, and alternative method is used to estimate lordosis. The Body Mass Index (BMI) is used to estimate obesity and the probability that the contour is obscured due to body fat. If BMI is greater than 25 kg/m$^2$, pelvic angle is used to estimate lordosis. A normal pelvic angle of 10° has been shown to be approximately equal to the normal lordotic angle of 32°, and increases in pelvic angle from normal are related to increases in lordosis.

If $BMI>25$ then $Ld°=Pa°+22°$

Body Mass Index (BMI) is calculated by taking the subject's weight in kilograms and dividing it by the height in meters squared. The formula is $$\frac{\text{mass (kg)}}{\text{height (m)}^2}$$

Head angle (Ha°) is measured from the flat marker placed on the tragus to spherical marker placed on C7 relative to vertical plumb.

Pelvic angle (Pa°) is measured from the spherical markers placed on PSIS and ASIS and relative to horizontal plumb.

The head angle, kyphosis measure and lordosis/pelvis angle measures will be applied to an expert database and two indices will be formed that indicates the risk of osteoporosis and the risk of fracture associated with osteoporosis.

Osteoporosis Postural Index (OPIX)

As mentioned above, a series of postural measures is made from the lateral digital photograph and contour definition (utilizing anatomical markers). The information obtained is used to calculate an Osteoporosis Postural Index (OPIX). The components of the OPIX will be:

Head angle: The value given is Ha°−40°. Positive values indicate head is forward and negative values indicate head is posterior. Normal angle is 40°.

Kyphosis: The value given is Kr°−37°, Positive values indicate increases in Kyphosis, and negative values hypokyphosis. Normal kyphotic curve is 37°.

Lordosis: The value given is Ld°−32°. Positive values indicate hyper-lordosis (increase in lordosis) and negative values indicate hypo-lordosis (decrease in lordosis). Normal lordotic angle is 32°.

Pelvic angle: The value given is Pa°−10°. Positive values indicate anterior pelvic tilt and negative values indicate posterior pelvic tilt. Normal pelvic angle is 10°.

Risk Indices

The values used to identify body alignment and posture are combined with other measured variables to form two risk indices: the Osteoporosis Risk Index and the Osteoporosis Fracture Index. Different "weightings" of these variables are used to provide personalized risk assessments for these two fundamental components of osteoporosis. The variables are: Posture, age, height change, sex and BMI.

Osteoporosis Risk Index

In a preferred embodiment of the present invention, the relative "weights" or percentages of these factors for the Osteoporosis Risk Index are Age (35%), Posture (30%), BMI (20%) and Height Change (15%).

The Osteoporosis risk factor is obtained by the formula:

Osteoporosis risk factor=((Age factor×0.35)+(Posture factor×0.30)+(Height Change factor×0.15))× BMI factor The osteoporosis risk factor is a number between 0 and 100 with higher numbers indicating greater risk of osteoporosis. This is in turn converted to a color scale from green (low risk values) to red (high risk values) on an assessment report as illustrated in FIG. 3.

Age Factor

After 35, bone mineral density decreases by 0.4% per year until age 45, past 45, the rate of bone density decrease is 2% per year. Normal Bone mass in females is 1.2 g/cm$^2$, mild bone loss is 1.05 to 1.19, moderate is 0.91 to 1.04 and severe is 0.75 to 0.90 g/cm$^2$. From normal to severe, there is a 0.3 g/cm$^2$ or a decrease in 25% bone density. Normal bone mass is estimated in males to be 2.1 g/cm$^2$. From normal to severe, there is a 1.2 g/cm$^2$ or a decrease in 57% in bone mass density in males. Table 1 is listing the age factor coefficients and their conditions:

TABLE 1

| Age factor coefficients | |
|---|---|
| Age Factor | Conditions |
| 0 | Female and age ≦35 |
| $\frac{(\text{subject age} - 35) \times 0.4}{25} \times 100$ | Female and age >35 and ≦45 |
| $\frac{(\text{subject age} - 45) \times 2 + 4.4}{25} \times 100$ | Female and age >45 and ≦55 |
| 100 | Female and age is >55 |
| 0 | Male and age ≦35 |
| $\frac{(\text{subject age} - 35) \times 0.4}{57} \times 100$ | Male and age >35 and ≦45 |
| $\frac{(\text{subject age} - 45) \times 2 + 4.4}{57} \times 100$ | Male and age >45 and ≦72 |
| 100 | Male and age is >72 |

Posture Factor

A postural component score is formed with different weights provided for the different measures described above. Head angle contributes for 25% of the postural factor, Kyphosis contributes for 50% of the postural factor, Lordosis contributes for 13% of the postural factor and Pelvic angle contributes for 12% of the postural factor.

Normal Ha° is 35° and maximum Ha° is 45°. The greater the head angle, the greater the risk of low bone density (see formulas P1 below).

Normal Ky° is 37 and maximum Ky° is 80°. Greater Ky° indicates a greater risk of low bone density (see formulas P2 below).

Normal Ld° is 32°, maximum Ld° is 56° and minimum is 3°. The further Ld° deviates from 32° (either in the positive or negative direction) the greater the risk of low bone density (see formulas P3 below).

Normal Pa° is 10°, maximum Pa° is 32° and minimum is −9°. The further Pa° deviates from 10° (in the positive or negative directions) the greater the risk of low bone density (see formulas P4 below).

Table 2 lists the formulas for calculating the Head angle element of the postural factor.

TABLE 2

| Head angle element of postural factor | |
|---|---|
| Head Angle | P1 Formula |
| Ha° ≦35 | 0 |
| Ha° >35° and ≦45° | $\frac{(\text{Ha}° - 35)}{10} \times 100$ |
| Ha° >45° | 100 |

Table 3 lists the formulas for calculating the Kyphosis element of the postural factor.

TABLE 3

| Kyphosis element of postural factor | |
|---|---|
| Kyphosis | P2 Formula |
| Ky° ≦37° | 0 |
| Ky° >37° and ≦80° | $\frac{(\text{Ky}° - 37)}{43} \times 100$ |
| Ky° >80° | 100 |

Table 4 lists the formulas for calculating the Lordosis element of the postural factor.

TABLE 4

| Lordosis element of postural factor | |
|---|---|
| Lordosis | P3 Formula |
| Ld° <3 | 100 |
| Ld° ≧3° and <32° | $\frac{(32 - \text{Ld}°)}{29} \times 100$ |
| Ld° = 32° | 0 |
| Ld° >32 and ≦56° | $\frac{(\text{Ld}° - 32)}{24} \times 100$ |
| Ld° >56° | 100 |

Table 5 lists the formulas for calculating the Pelvic angle element of the postural factor.

TABLE 5

| Pelvic angle element of postural factor | |
|---|---|
| Pelvic angle | P4 Formula |
| Pa° <−9° | 100 |
| Pa° ≧−9° and <10° | $\frac{(10 - \text{Pa}°)}{18} \times 100$ |
| Pa° = 10° | 0 |
| Pa° >10 and ≦32° | $\frac{(\text{Pa}° - 10)}{22} \times 100$ |
| Pa° >32° | 100 |

The Posture factor is finally calculated from the formula:

Posture factor=(P1×0.25)+(P2×0.5)+(P3×0.13)+(P4×0.12)

Height Change Factor

Height loss is indicative of osteoporosis and kyphosis is related to height loss. To estimate the potential height change associated with osteoporosis, the following method is used. If the kyphotic angle (Ky°) is greater than 37°, measured height increase 0.267 cm for every 1° increase in kyphosis past 37°. If the kyphosis angle is less than 37°, no adjustment is made to measured height. Kyphosis has a maximum impact on height loss of 11 cm, consequently, measured height is adjusted to a maximum of 11 cm. The maximum amount of kyphosis is 80°, and normal is 37°, giving a difference of 43°, converted to height loss in cm of 11.

Table 6 lists the formulas for calculating the baseline height element of the height change factor.

TABLE 6

Baseline height element of the height change factor

| Ky | Baseline height |
|---|---|
| Ky° ≦37° | measured height |
| Ky° >37° | $\frac{(Ky° - 37) \times 4}{15}$ + measured height |

The Height change factor is calculated from the following formula:

$$\text{Height change factor} = \frac{(\text{Baseline height} - \text{measured height})}{11} \times 100$$

BMI Factor

The BMI factor is applied to the previously calculated variables. Low BMI is related to low bone mass and higher risk of osteoporosis. If females have a BMI below 25 kg/m², risk increases by 25.3%. If males have a BMI below 27 kg/m², risk increases by 25.3%.

Table 7 lists the BMI factors depending on the patient's BMI.

TABLE 7

BMI factors

| BMI | BMI factors |
|---|---|
| BMI ≦ 25 kg/m² for females | 1.25 |
| BMI > 25 kg/m² for females | 1 |
| BMI ≦ 27 kg/m² for males | 1.25 |
| BMI > 27 kg/m² for males | 1 |

Fracture Risk Index

The Fracture risk index is calculated similarly to the Osteoporosis Risk Index but with different "weights" for the factors. Postural variables are highly predictive of fracture related to osteoporosis. Age will represent 15%, posture represents 50%, BMI represents 20% and Height change represents 15% of the fracture risk index. The formula for calculating of the Fracture risk index is the following:

Fracture risk index=((Age factor×0.15)+(Posture factor×0.50)+(Height Change factor×0.15))×*BMI* factor The fracture risk index is a number between 0 and 100 with higher numbers indicating greater risk of fracture, as for example a neck fracture or a hip fracture. This is converted to a color scale from green (low risk values) to red (high risk values) on an assessment report as illustrated in FIG. 3.

Assessment Report

In a preferred embodiment of the present invention, an assessment report as illustrated in FIG. 3 is provided to the patient. This report contains the following components:

Lateral view photographs of the patient with head angle and pelvic angles and spinal curvature (showing kyphosis and/or lordosis) highlighted and compared to normal spinal curvature.

The Osteoporosis Postural Index. The key postural indicators of Osteoporosis are shown and compared to normal values.

The Osteoporosis Risk Index and the Fracture Risk Index are presented with color scaling to indicate risk status. Measures in the "green" area are considered as acceptable, measures in the "yellow" area are indicating a moderate risk (with a follow up OsteoPrint to be scheduled annually), and measures in the "red" area are indicating an immediate risk. For measures in the "yellow" or "red" areas, corrective or preventative exercises can be provided.

A tracking feature shows the progression of the subject's posture based on the spine extrapolated from the photo taken at the annual evaluations.

Exercise Progression Logic

The programs are prescribed with the approval of the patient's primary physician and/or physical therapist and the programs are preferably performed with all sessions beginning with a warm-up. The warm-up preferably consists of weight bearing activity (stair climbing, beginner step class, low impact aerobics, walking) that elevates the patient's heart rate slightly (refer to heart rate tables) for preferably 10 minutes. Moderate muscle fatigue should occur after 10–15 repetitions when performing the strengthening exercises. If it does not, it is preferable to increase the amount of applied resistance (no more than %10 increase each week)

Contraindicated movements/exercises for an individual with osteoporosis include: trunk flexion, trunk rotation, trunk lateral flexion and the patient should avoid rowing machines.

Strengthening is preferably submaximal, incorporating the major muscle groups and performed as tolerated by the individual patient.

Three types of exercise are particularly recommended for osteoporosis at risk patients: Low bone density exercise (impact exercise), postural exercises and preventative strengthening exercises (maintenance program incorporating the major muscle groups)

The programs can be supervised exercise (SE), non-supervised exercise (NS), equipment based exercise (EE), or home based (HE).

In a program, different combinations of types of programs can be used. Table 8 is providing examples of exercises for different combinations.

TABLE 8

Combinations and examples of exercises

| Combination | Examples of exercises |
|---|---|
| SE/EE/Low bone density exercise | treadmill, stairmaster with a personal trainer or supervised |
| SE/EE/postural exercise | Pulley machines and free weights |

TABLE 8-continued

Combinations and examples of exercises

| Combination | Examples of exercises |
|---|---|
| SE/EE/maintenance exercise | with a personal trainer or supervised Free weights, equipment, large muscle group exercises with a personal trainer or supervised |
| SE/HE/Low bone density exercise | Group power walk, step class led by an instructor |
| SE/HE/postural exercise | Supervised posture exercises with or without dumbbells and/or elastic resistance |
| SE/HE/maintenance exercise | Supervised maintenance exercises with or without dumbbells and/or elastic resistance |
| NS/EE/Low bone density exercise | treadmill, stairmaster, no supervision |
| NS/EE/postural exercise | Pulley machines and free weights no supervision |
| NS/EE/maintenance exercise | Free weights, equipment, large muscle group exercises with no supervision |
| NS/HE/Low bone density exercise | Speed walking, stairclimbing, stepping with no supervision |
| NS/HE/postural exercise | Postural exercises with or without dumbbells and/or elastic resistance, no supervision |
| NS/HE/maintenance exercise | Maintenance exercises with or without dumbbells and/or elastic resistance, no supervision |

Patients with a low risk of osteoporosis/fracture are preferably exercising in a very similar manner than in regular exercise prescription (however, careful with patient positioning during the execution of each exercise)

Strength Exercises
10–15 repetitions
2–3 sets
Perform 3–4 times per week
Flexibility
Hold each stretch for 30 seconds and repeat 3 times Patients with a moderate risk of osteoporosis/fracture are preferably exercising with a lower intensity, conservative exercise prescription than that normally given to a healthy population. Careful consideration is given to patient positioning during the execution of each exercise Strength Exercises
10–15 repetitions
2 sets
Perform exercises every third day
Flexibility
Hold each stretch for 30 seconds and repeat 3 times Patients with a high risk of osteoporosis/fracture are preferably exercising with a very low intensity and more conservative exercise prescription than normally given to a healthy population. Careful consideration is given to patient positioning during the execution of each exercise.

Strength Exercises
10–15 repetitions (as tolerated by the individual patient).
1–2 sets
Perform exercises every third day (Katz, 1998.)
Flexibility
Hold each stretch for 30 seconds and repeat 3 times There is provided examples of unsupervised, home-based exercise progressions for four potential deviations. The deviations are the following: Forward head position, thoracic kyphosis, lumbar hyperlordosis and lumbar hypolordosis.

These exercise programs have been designed to be of 10 weeks duration, which is comprised of three sessions respectively. The first session are of 4 weeks in duration, the second and third sessions are both be three weeks long, respectively.

EXAMPLE 1

Mild Osteoporosis Risk

| Deviation | Target Areas/ Exercises | Session# | Name of exercise to be linked |
|---|---|---|---|
| Forward head | Chin tuck | 1: | Standing chin tuck |
| | | 2: | Lying chin tuck |
| | | 3: | Lying chin tuck |
| Kyphosis | rowing (scapula) | 1. | Standing, bilateral rowing with elastic resistance |
| | | 2. | Prone, on a bench, rowing with weight |
| | | 3. | Prone, on a bench, rowing with weight |
| | external shoulder rotation | 1. | Seated with elastic resistance |
| | | 2. | Side lying on floor or bench with weight |
| | | 3. | Side lying on floor or bench with weight |
| | trunk extension (lift primarily the upper chest off the floor) | 1. | Back extension with pillow under hips arms by your side |
| | | 2. | Back extension with pillow under hips arms beside your head |
| | | 3. | Back extension with pillow under hips hands holding weight |
| | cobra (keep elbows on the floor) | | Chest lift elbows on the floor (all sessions) |
| | pec stretch | 1. | Unilateral chest stretch |
| | | 2. | Chest stretch in a doorframe |
| | | 3. | Chest stretch in a doorframe |
| hyperlordosis | abs | | abdominal hollowing (isometric) all sessions |
| | Hip extensor strengthening | 1. | bridge |
| | | 2. | Prone on bench or floor leg straight |
| | | 3. | Prone on bench or floor bent knee with weight |
| | Hip flexor stretch | 1. | Lunge stretch holding a chair |
| | | 2. | Standing quad stretch holding a chair |
| | | 3. | Side-lying quad stretch |
| | Lower back stretch | | Supine, knees to chest (all sessions) |
| hypolordodis | back extension | 1. | Back extension with pillow under hips, arms by your side |
| | | 2. | Back extension with pillow under hips, arms beside your head |
| | | 3. | Back extension with pillow under hips, hands holding weight |
| | strengthen quads and hip flexors | 1. | Seated knee lifts with weight (in a chair) |

-continued

| Deviation | Target Areas/Exercises | Session# | Name of exercise to be linked |
|---|---|---|---|
|  |  | 2. | Standing leg lift front with weight |
|  |  | 3. | Standing leg lift front with elastic |
|  | cobra |  | Chest lift elbows on the floor (all sessions) |
|  | Hamstring stretch |  | Supine, on the floor with a towel around the foot (all sessions) |

EXAMPLE 2

Moderate Osteoporosis Risk

| Deviation | Target Areas/Exercises | Session# | Name of exercise to be linked |
|---|---|---|---|
| Forward head | Chin tuck | 1: | standing chin tuck |
|  |  | 2: | Lying chin tuck |
|  |  | 3: | Lying chin tuck |
| Kyphosis | Rowing (scapula) | 1. | Prone on the floor arms bent beside your head |
|  |  | 2. | standing bilateral rowing with elastic resistance |
|  |  | 3. | prone on a bench rowing with weight |
|  | external shoulder rotation | 1. | Seated with elastic resistance |
|  |  | 2. | Seated with elastic resistance |
|  |  | 3. | Side lying on floor or bench with weight |
|  | trunk extension (lift primarily the upper chest off the floor | 1. | Back extension with arm assistance |
|  |  | 2. | Back extension with pillow under hips arms by your side |
|  |  | 3. | Back extension with pillow under hips arms beside your head |
|  | cobra (keep elbows on the floor) |  | Chest lift elbows on the floor (all sessions) |
|  | Pec stretch | 1. | Supine, arms out to the side palms up |
|  |  | 2. | Unilateral chest stretch |
|  |  | 3. | Bilateral in a doorframe |
| hyperlordosis | Abs |  | abdominal hollowing (isometric) all sessions |
|  | Hip extensors | 1. | Bridge (very low) |
|  |  | 2. | Bridge |
|  |  | 3. | Prone on bench or floor leg straight |
|  | Hip flexor stretch | 1. | Lunge stretch holding a chair |
|  |  | 2. | Lunge stretch holding a chair |
|  |  | 3. | Standing quad stretch holding a chair |
|  | Lower back stretch |  | Supine, knees to chest (all sessions) |
| hypolordodis | Back extension | 1. | Back extension with arm assistance |
|  |  | 2. | Back extension with pillow under hips arms by your side |
|  |  | 3. | Back extension with pillow under hips arms beside your head |
|  | Hip flexor strengthening | 1. | Seated knee lifts with weight (in a chair) |
|  |  | 2. | Standing leg lift front with elastic resistance |
|  |  | 3. | Standing leg lift front with weight |
|  | Cobra (elbows on the floor) |  | Chest lift elbows on the floor (all sessions) |
|  | Hamstring stretch |  | Supine, on the floor with a towel around the foot (all sessions) |

EXAMPLE 3

High Osteoporosis Risk

| Deviation | Target Areas/Exercises | Session# | Name of exercise to be linked |
|---|---|---|---|
| Forward head | Chin tuck | 1: | Lying chin tuck |
|  |  | 2: | Lying chin tuck |
|  |  | 3: | Lying chin tuck |
| Kyphosis | Rowing (scapula) | 1. | Prone on the floor arms bent beside your head |
|  |  | 2. | Prone on the floor arms bent beside your head |
|  |  | 3. | standing bilateral rowing with elastic resistance |
|  | external shoulder rotation | 1. | Side lying no weight |
|  |  | 2. | Seated with elastic resistance |
|  |  | 3. | Seated with elastic resistance |
|  | Trunk extension | 1. | Back extension with arm assistance |
|  |  | 2. | Back extension with arm assistance |
|  |  | 3. | Back extension with pillow under hips arms by your side (if capable) |
|  | Pec stretch | 1. | Supine, arms out to the side palms up |
|  |  | 2. | Supine, arms out to the side palms up |
|  |  | 3. | Unilateral chest stretch |
| hyperlordosis | Abs |  | abdominal hollowing (isometric) all sessions |
|  | Hip extensor strengthening | 1. | Isometric hip squeeze |
|  |  | 2. | Bridge (very low) |
|  |  | 3. | Bridge (very low) |
|  | Hip flexor stretch | 1. | Lunge stretch holding a chair |
|  |  | 2. | Lunge stretch holding a chair |
|  |  | 3. | Lunge stretch holding a chair |
|  | Lower back stretch |  | Supine, knees to chest (all sessions) |
| hypolordodis | Back extension | 1. | Back extension with arm assistance |
|  |  | 2. | Back extension with arm assistance |
|  |  | 3. | Back extension with |

-continued

| Deviation | Target Areas/ Exercises | Session# | Name of exercise to be linked |
|---|---|---|---|
| | | | pillow under hips arms by your side (if capable) |
| | Hip flexor strengthening | 1. | Seated knee lifts no weight (in a chair) |
| | | 2. | Seated knee lifts with weight (in a chair) |
| | | 3. | Standing leg lift front with weight (if tolerated otherwise no weight) |
| | Hamstring stretch | | Supine, on the floor with a towel around the foot (all sessions) |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for determining a risk value of developing a skeletal condition in a patient, the method comprising steps of:
   a) taking at least one picture of said patient and obtaining position data from said picture identifying a position in space of body landmarks of the upper body of a patient while standing relaxed and in normal posture;
   b) establishing a relationship between risk of developing a skeletal condition and a plurality of factors including posture;
   c) calculating at least two of head angle, thoracic curve, lumbar curve and pelvis tilt angle deviation values of said patient using the position data; and
   d) calculating said risk of developing a skeletal condition using said angle deviation values and said relationship.

2. The method of claim 1, wherein said skeletal condition is fracture.

3. The method of claim 2, wherein said fracture is selected from the group consisting of neck fracture and hip fracture.

4. The method of claim 2, wherein said relationship is ((Age factor×0.15)+(Postural factor×0.50)+(Height Change factor×0.15))×BMI factor.

5. The method of claim 4, wherein said postural factor is calculated in a manner in which head angle contributes for about 25% of the postural factor, kyphosis contributes for about 50% of the postural factor, lordosis contributes for about 13% of the postural factor and pelvic angle contributes for about 12% of the postural factor.

6. The method of claim 1, wherein said body landmarks are tragus, acromion, C7 vertebrae, T5 vertebrae, anterior-superior iliac spine and posterior-superior iliac spine.

7. The method of claim 6, wherein a flat marker is placed on the tragus and spherical markers are placed on the acromion, C7 vertebrae, T5 vertebrae, anterior-superior iliac spine and posterior-superior iliac spine.

8. The method of claim 1, wherein said at least one picture is a lateral view of said patient.

9. The method of claim 1, wherein said angle deviations calculated are head angle, thoracic curve or kyphosis, lumbar curve or lordosis, and pelvis tilt.

10. The method of claim 9, wherein said angle deviation values are referenced with respect to average values.

11. The method of claim 9, wherein said skeletal condition is osteoporosis.

12. The method of claim 9, wherein step (de) includes calculating a postural factor in which head angle contributes for about 25% of the postural factor, kyphosis contributes for about 50% of the postural factor, lordosis contributes for about 13% of the postural factor and pelvic angle contributes for about 12% of the postural factor.

13. The method of claim 12, further comprising calculating a body mass index (BMI) for the patient, and determining lordosis angle to be pelvic angle plus about 22 degrees when BMI is greater than about 25kg per m$^2$.

14. The method of claim 1, wherein said skeletal condition is osteoporosis.

15. The method of claim 14, wherein said relationship is ((Age factor×0.35)+(Postural factor×0.30)+(Height Change factor×0.15))×BMI factor.

16. The method of claim 15, wherein said postural factor Is calculated in a manner in which head angle contributes for about 25% of the postural factor, kyphosis contributes for about 50% of the postural factor, lordosis contributes for about 13% of the postural factor and pelvic angle contributes for about 12% of the postural factor.

17. A method of selecting exercises for reducing risk to develop a skeletal condition in a patient, the method comprising the steps of:
   a) obtaining angle deviations of body part of a patient indicative of a risk to develop a skeletal condition, said angle deviations comprising at least two from the group consisting of head angle, thoracic curve, lumbar curve and pelvis tilt;
   b) correlating angle deviations with exercises for strengthening or stretching specific muscles or muscle groups;
   c) compiling an exercise program based on the exercises provided in step b).

18. The method of claim 17, wherein the step of compiling comprises manually selecting exercises from a list of exercises.

19. The method of claim 17, wherein said skeletal condition is selected from the group consisting of osteoporosis and fracture.

20. The method of claim 19, wherein said fracture is selected from the group consisting of neck fracture and hip fracture.

21. The method of claim 17, wherein said angle deviations comprise head angle, thoracic curve, lumbar curve and pelvis tilt.

22. An apparatus for estimating skeletal condition risk in a patient comprising:
   a) a position data acquisition device for identifying a position in space of body landmarks of an upper body of the patient while standing relaxed and in normal posture;
   b) an angle of deviation calculator for determining angle deviation values of body parts being indicative of a skeletal condition risk using the position data, said angle deviations comprising at least two from the group consisting of head angle, thoracic curve, lumbar curve and pelvis tilt; and
   c) a calculator adapted to calculate a value for said risk using a relationship between said risk and a plurality of factors including said angle deviation values.

23. The apparatus of claim 22, wherein said skeletal condition is selected from the group consisting of osteoporosis arid fracture.

24. The apparatus of claim 23, wherein said fracture is selected from the group consisting of neck fracture and hip fracture.

25. The apparatus of claim 22, wherein said angle deviation value is with respect to average or normal value.

26. An apparatus for selecting exercises for reducing risk to develop a skeletal condition in a patient comprising:
   a) an angle of deviation device for obtaining angle deviations of an upper body part of a patient being indicative of a risk to develop a skeletal condition, said angle deviations comprising at least two from the group consisting of head angle, thoracic curve, lumbar curve and pelvis tilt;
   b) a correlator for correlating angle deviations with exercises for strengthening or stretching muscles or muscle groups;
   c) a compiler for compiling an exercise program based on the exercises provided in step b).

* * * * *